(12) United States Patent
Nozawa (10) Patent No.: US 8,264,767 B2
(45) Date of Patent: Sep. 11, 2012

(54) SURGICAL OBSERVATION SYSTEM (75) Inventor: Junichi Nozawa, Sagamihara (JP)

(73) Assignee: Olympus Medical Systems Corp. (JP)

( * ) Notice: Subject to any disclaimer, the term of this patent is extended or adjusted under 35 U.S.C. 154(b) by 824 days.

(21) Appl. No.: 12/299,694

(22) PCT Filed: Jan. 16, 2008

(86) PCT No.: PCT/JP2008/050441
§ 371 (c)(1),
(2), (4) Date: Nov. 5, 2008

(87) PCT Pub. No.: WO2008/120479
PCT Pub. Date: Oct. 9, 2008

(65) Prior Publication Data
US 2009/0103174 A1    Apr. 23, 2009

(30) Foreign Application Priority Data

Mar. 29, 2007    (JP) ................... 2007-087755

(51) Int. Cl.
G02B 21/00    (2006.01)
G02B 21/18    (2006.01)
(52) U.S. Cl. ............ 359/381; 359/368; 359/372
(58) Field of Classification Search ....... 359/368–390, 359/656–661, 821
See application file for complete search history.

(56) References Cited

U.S. PATENT DOCUMENTS 4,364,629 A * 12/1982 Lang et al. ............. 359/377
5,095,887 A * 3/1992 Leon et al. ............. 600/166
6,020,996 A * 2/2000 Perkins et al. .......... 359/399
7,122,032 B2 * 10/2006 Shinmura et al. ......... 606/34
2003/0069471 A1 * 4/2003 Nakanishi et al. ........ 600/101

FOREIGN PATENT DOCUMENTS

| JP | 55-155642 | 12/1980 |
| JP | 06-167658 | 6/1994 |
| JP | 2005-134537 | 5/2005 |
| JP | 2006-061272 | 3/2006 |

OTHER PUBLICATIONS

International Search Report mailed Feb. 26, 2008 in corresponding PCT International Application No. PCT/JP2008/050441.

* cited by examiner

*Primary Examiner* — Thong Nguyen
(74) *Attorney, Agent, or Firm* — Ostrolenk Faber LLP (57) ABSTRACT

A surgical observation system provided with a supporting arm movable in the three-dimensional direction includes an endoscope objective unit having a tubular insertion section and provided with objective optical systems, a microscope objective unit provided with objective optical systems having a focusing optical system and variable magnification optical systems, and a mounting and dismounting section provided in the supporting arm, mountable and dismountable with respect to the objective units by having interchangeability. The objective optical systems provided in each of the objective units are constructed so that light beams emerging therefrom toward the mounting and dismounting section are changed to afocal light beams, and the mounting and dismounting section is provided with a pair of imaging lenses and a pair of image sensors and is constructed so that, in a state where the objective unit is mounted to the mounting and dismounting section, the objective unit is optically connected with the mounting and dismounting section.

6 Claims, 8 Drawing Sheets

$a1 = a2$
$\theta 1 = \theta 2$

ns system in
SURGICAL OBSERVATION SYSTEM

CROSS-REFERENCE TO RELATED APPLICATIONS

The present application is a 35 U.S.C. §§371 national phase conversion of PCT/JP2008/050441, filed Jan. 16, 2008, which claims priority of Japanese Patent Application No. 2007-087755, filed Mar. 29, 2007, the disclosure of which has been incorporated herein by reference. The PCT International Application was published in the Japanese language.

TECHNICAL FIELD

This invention relates to a surgical observation system in which when a surgical operation is performed, the observation of an operative part is carried out from a desired position with an observation apparatus through a supporting arm movable in a three-dimensional direction.

BACKGROUND ART

In a surgical operation, for example, in a neurosurgical operation, a detailed condition of a minute operative part on the surface of a brain is observed under a microscope and thereby the surgical operation is performed. In recent years, the surgical operation in which an endoscope inserted in the brain for the purpose of reducing the area of craniotomy is used has also been performed.

However, when both a surgical endoscope and a surgical microscope are individually arranged in an operating room, the space of the operating room is limited. Hence, in the surgical operation, for example, of neurosurgery, it becomes necessary to provide an observation apparatus switchable between a microscope observation and an endoscope observation without individually arranging both the surgical endoscope and the surgical microscope.

As conventional observation apparatuses constructed to be switchable between the microscope observation and the endoscope observation, stereoscopic observation apparatuses set forth, for example, in Japanese Patent Kokai Nos. Hei 6-167658 and 2005-134537 are available.

Each of the observation apparatuses described in Kokai Nos. Hei 6-167658 and 2005-134537 is designed to mount and dismount an endoscope to and from a microscope body and thereby to be switchable between the microscope observation (where the endoscope is dismounted) and the endoscope observation (where the endoscope is mounted).

In the surgical observation system, the observation apparatus for the endoscope or the microscope is supported by a supporting arm movable in a three-dimensional direction so that the observation apparatus is moved to a desired position and in a desired direction through the supporting arm by an operator in accordance with an operative condition and thereby the observation can be made. When the surgical observation system is used to perform the surgical operation, assistants are present in addition to the operator around a patient, and further a display device for displaying the image of an operative part, obtained through the observation apparatus, and various devices and tools used for the surgical operation are provided. Consequently, in order to make the observation apparatus hard to interfere with the operation assistants and the tools when the observation apparatus is moved to the desired position and in the desired direction by the operator in the surgical operation, it is important that the observation apparatus is designed to be the smallest possible size.

The observation apparatus set forth in Kokai No. Hei 6-167658, however, is constructed so that the endoscope is mounted to the top of the microscope body and thereby a changeover is made from the microscope observation to the endoscope observation. When the endoscope observation is thus carried out, an optical arrangement of the microscope body originally unnecessary for the endoscope remains as it is.

As a result, in the surgical observation system using the observation apparatus described in Kokai No. Hei 6-167658, when the endoscope observation is made, the observation apparatus is elongated in an observation direction and becomes oversize, and its maneuverability where the apparatus is moved through the supporting arm is deteriorated.

In the observation apparatus set forth in Kokai No. 2005-134537, a part of an optical path forming an intermediate imaging plane is bent in the interior of the endoscope. According to the observation apparatus set forth in Kokai No. 2005-134537, therefore, the size in the observation direction can be made smaller for the bent optical path than in the observation apparatus described in Kokai No. Hei 6-167658.

However, the observation apparatus set forth in Kokai No. 2005-134537, as well as the observation apparatus described in Kokai No. Hei 6-167658, is constructed so that the endoscope is mounted to the top of the microscope body and thereby the changeover is made from the microscope observation to the endoscope observation. When the endoscope observation is thus carried out, an optical arrangement of the microscope body originally unnecessary for the endoscope remains as it is.

As a result, even in the surgical observation system using the observation apparatus set forth in Kokai No. 2005-134537, when the endoscope observation is made, the observation apparatus is likewise elongated in the observation direction and becomes oversize although somewhat smaller than in the observation apparatus described in Kokai No. Hei 6-167658, and the deterioration of the maneuverability where the apparatus is moved through the supporting arm cannot be eliminated.

Furthermore, in the surgical observation system, when the observation apparatus is used to perform the surgical operation, it is necessary that a sterilization means for keeping off the infection of bacteria to a patient is used for the observation apparatus. In general, when the microscope surgical operation is performed, the microscope and the supporting arm supporting the microscope are covered with sterilization drapes. On the other hand, when the endoscope surgical operation is performed, the supporting arm supporting the endoscope is covered with the sterilization drape, and sterilization treatment, such as autoclaving or EOG, is applied to the endoscope.

However, each of the observation apparatuses set forth in Kokai Nos. Hei 6-167658 and 2005-134537, as mentioned above, is constructed so that when the endoscope observation is carried out, the endoscope is connected to the microscope body. Consequently, when the changeover is made between the microscope observation and the endoscope observation in the surgical operation, the sterilization drape covering the mounting portion of the microscope body must be mounted and dismounted each time the endoscope is mounted to, and dismounted from, the microscope body, and thus the surgical operation is interrupted accordingly and the operation time is extended. At the same time, changeover work from the microscope observation to the endoscope observation is complicated. Such interruption of the surgical operation and complication of the changeover work impose a mental load, such as stress, on the operator and a physical load on the patient.

SUMMARY OF THE INVENTION

It is, therefore, an object of the present invention to provide a surgical observation system in which even when the changeover is made between the microscope observation and the endoscope observation, the maneuverability obtained through the supporting arm can be favorably maintained and the manipulation of changeover between the microscope observation and the endoscope observation can be smoothly performed without interrupting the surgical operation.

In order to achieve the above object, the surgical observation system according to the present invention comprises an observation apparatus switchable between the endoscope observation and the microscope observation and a supporting arm movable in a three-dimensional direction in a state where the observation apparatus is supported. In this case, the observation apparatus is constructed to include an endoscope objective unit having a tubular insertion section and provided with objective optical systems; a microscope objective unit provided with objective optical systems having a focusing optical system and variable magnification optical systems; and a mounting and dismounting section provided in the supporting arm, having a mounting and dismounting port constructed so that the endoscope objective unit and the microscope objective unit are mountable and dismountable by having interchangeability. The objective optical systems provided in each of the endoscope objective unit and the microscope objective unit are constructed so that light beams emerging therefrom toward the mounting and dismounting section are changed to afocal light beams, and the mounting and dismounting section is provided with a pair of imaging lenses and a pair of image sensors and is constructed so that, in a state where the objective unit is mounted to the mounting and dismounting port of the mounting and dismounting section, the afocal light beams emerging from the objective unit are optically connected with the imaging lenses and the image sensors.

In the surgical observation system of the present invention, it is desirable that the supporting arm is provided with a sterilization drape mountable and dismountable, having an opening mountable on the periphery of the mounting and dismounting port in the mounting and dismounting section, and each of the endoscope objective unit and the microscope objective unit is constructed so that a sterilization means can be taken independently.

In the surgical observation system of the present invention, it is desirable that the objective optical systems provided in the endoscope objective unit and the objective optical systems provided in the microscope objective unit are constructed to be practically identical in exit pupil positions and exit field angles.

According to the present invention, the surgical observation system is obtained in which even when the changeover is made between the microscope observation and the endoscope observation, the maneuverability obtained through the supporting arm can be favorably maintained and the manipulation of changeover between the microscope observation and the endoscope observation can be smoothly performed without interrupting the surgical operation.

BEST MODE FOR CARRYING OUT THE INVENTION

Before undertaking the description of the embodiments, the function and effect of the present invention will be explained.

In the surgical observation system of the present invention, the microscope objective unit and the endoscope objective unit are constructed to be mountable and dismountable by having interchangeability in respect of the mounting and dismounting section including imaging optical systems and image sensors.

In this way, when the microscope observation is switched to the endoscope observation, the optical arrangement of the microscope objective unit originally unnecessary for the endoscope observation does not remain. According to the surgical observation system of the present invention, therefore, when the endoscope observation is carried out, the length in the observation direction is materially reduced so that a compact design can be achieved, and the maneuverability where the apparatus is moved through the supporting arm can be exceptionally improved, in contrast with the conventional observation apparatuses such as those described in Kokai Nos. Hei 6-167658 and 2005-134537.

When the microscope objective unit and the endoscope objective unit are constructed to be mountable and dismountable by having interchangeability in respect of the mounting and dismounting section including the imaging optical systems and the image sensors, a sterilization drape having an opening mountable on the periphery of the mounting and dismounting port in the mounting and dismounting section can be provided to be mountable and dismountable, and a sterilization means can be used independently for each of the endoscope objective unit and the microscope objective unit.

In this way, when the changeover from the microscope observation to the endoscope observation is performed, it becomes unnecessary to remove the drape covering the mounting and dismounting section, unlike the conventional observation apparatuses such as those described in Kokai Nos. Hei 6-167658 and 2005-134537. Hence, the changeover work is not complicated, and there is no need to interrupt the surgical operation.

Also, as the sterilization means, sterilization treatment, such as autoclaving or EOG is considered with respect to each of the endoscope objective unit and the microscope objective unit. Also, provisions may be made for applying the sterilization treatment, such as autoclaving or EOG to the endoscope objective unit and for using a sterilization cover, to be mountable and dismountable, in the microscope objective unit.

Even in the above description, when the microscope observation is switched to the endoscope observation, the microscope objective unit is removed from the mounting and dismounting section, with the sterilization cover mounted without removing it from the microscope objective unit, and the endoscope objective unit can be mounted to the mounting and dismounting section. Hence, the changeover work can be smoothly done without complication and there is no need to interrupt the surgical operation.

In general, the insertion section of the endoscope is configured into the shape of a tube with a small diameter which can be inserted in the body, and the endoscope objective optical system has an optical path inside this tubular insertion section. Preset optical members are provided in the optical path. Here, in the endoscope provided with a pair of endoscope objective optical systems with parallax in order to make a three-dimensional observation, a pair of optical paths is provided inside the tubular insertion section which is small in diameter, and optical members provided in the pair of optical paths are such that a spacing between their optical axes is extremely narrow.

On the other hand, in the microscope, a pair of microscope objective optical systems with parallax for making the three-dimensional observation is not inserted in the body, and thus the spacing between mutual optical axes is wider by far than in the endoscope.

Consequently, the endoscope is very different from the microscope in spacing between the optical axes of a pair of objective optical systems for making the three-dimensional observation.

However, the surgical observation system of the present invention is such that, in a state where the objective unit is mounted to the mounting and dismounting port of the mounting and dismounting section, afocal light beams emerging from the objective unit can be optically connected with the imaging optical systems and the image sensors. It is good practice that, for example, the objective optical systems in the endoscope objective unit are constructed as a pair of endoscope objective optical systems having a pair of optical paths in the tubular insertion section, and, for example, parallelogram prisms are arranged on the mounting and dismounting section side of the tubular insertion section to widen the spacing between mutual optical axes so that, in a state where the endoscope objective unit is mounted to the mounting and dismounting port of the mounting and dismounting section, a pair of afocal light beams emerging from the pair of endoscope objective optical systems is optically connected with a pair of imaging optical systems and a pair of image sensors provided in the mounting and dismounting section.

On the other hand, it is good practice that the objective optical systems of the microscope objective unit are constructed as a pair of microscope objective optical systems including a focusing optical system placed in common with two optical paths with parallax and a pair of variable magnification optical systems arranged in the two optical paths with parallax so that, in a state where the microscope objective unit is mounted to the mounting and dismounting port of the mounting and dismounting section, a pair of afocal light beams emerging from the pair of microscope objective optical systems is optically connected with the pair of imaging optical systems and the pair of image sensors provided in the mounting and dismounting section.

In general, the endoscope is different from the microscope in the working distance and field angle of the objective optical system and the exit pupil position and exit angle of the afocal light beam emerging from the objective optical system.

However, in the present invention, if the endoscope objective unit is different from the microscope objective unit in the exit pupil position and exit angle of the afocal light beam emerging from each of the objective optical systems, the imaging area of the light beam where each objective unit is mounted to the mounting and dismounting section of the supporting arm varies and does not coincide with the imaging region on each image sensor, with the result that an image loss is caused.

Thus, in order to prevent such a loss, it is good practice that, in the surgical observation system of the present invention, even when either of the objective units is mounted to the supporting arm, a means making adjustment so that the area of the image formed on each image sensor has a preset size is provided in the mounting and dismounting section. For example, in the mounting and dismounting section, it is desirable that a pair of afocal variable magnification optical systems is provided on the object side of the pair of imaging optical systems, and afocal light beams in which the objective optical systems of the endoscope objective unit are different in magnification from the objective optical systems of the microscope objective unit can be adjusted to equalize the areas of images formed on the pair of image sensors through the pair of imaging optical systems.

In the present invention, it is also desirable that the objective optical systems provided in the endoscope objective unit and the microscope objective unit are constructed so that their exit pupil positions and exit field angles are practically identical. By doing so, whenever the afocal variable magnification optical systems are arranged in the mounting and dismounting section as mentioned above and a desired objective unit is mounted to the supporting arm, there is no need to adjust the light beams so that the areas of images formed on the image sensors coincide, and the changeover between the microscope observation and the endoscope observation can be smoothly performed.

Further, in the surgical observation system of the present invention, it is desirable that the endoscope objective unit is designed so that the objective optical systems are constructed as a pair of objective optical systems of different observation ranges in size and a pair of afocal light beams emerging from the pair of objective optical systems is optically connected to the pair of imaging optical systems and the pair of image sensors arranged in the mounting and dismounting section.

Specifically, it is desirable that, for example, of the pair of objective optical systems of different observation ranges in size, arranged in the endoscope objective unit, an objective optical system of a narrow observation range is constructed as the endoscope objective optical system having the tubular insertion section. It is also desirable that an objective optical system of a wider observation range is constructed to have the field angle at which the top of the tubular insertion section in the endoscope objective optical system of the narrow observation range can be viewed and to lie in the proximity of the mounting and dismounting section in the endoscope objective unit. In this way, an internal micro observation and an external macro observation in the two-dimensional observation can be carried out in such a way that, for example, a relative positional relationship between an internal affected part and the insertion section of the endoscope and the condition of the internal affected part are displayed on a display screen and observed at the same time.

Alternatively, the pair of objective optical systems of different observation ranges in size, arranged in the endoscope objective unit may be constructed to include a single optical system provided with a single optical path in the tubular insertion section, a path splitting member placed on the mounting and dismounting section side of the tubular insertion section, and an optical system narrowing the observation range, placed on one optical path split through the path splitting member.

In this way, the internal micro observation and the external macro observation in the two-dimensional observation can be carried out in such a way that, for example, two images, of the affected part, with different observation ranges in size are displayed on a display screen and observed at the same time in an observable range.

First Embodiment

Figure 1:
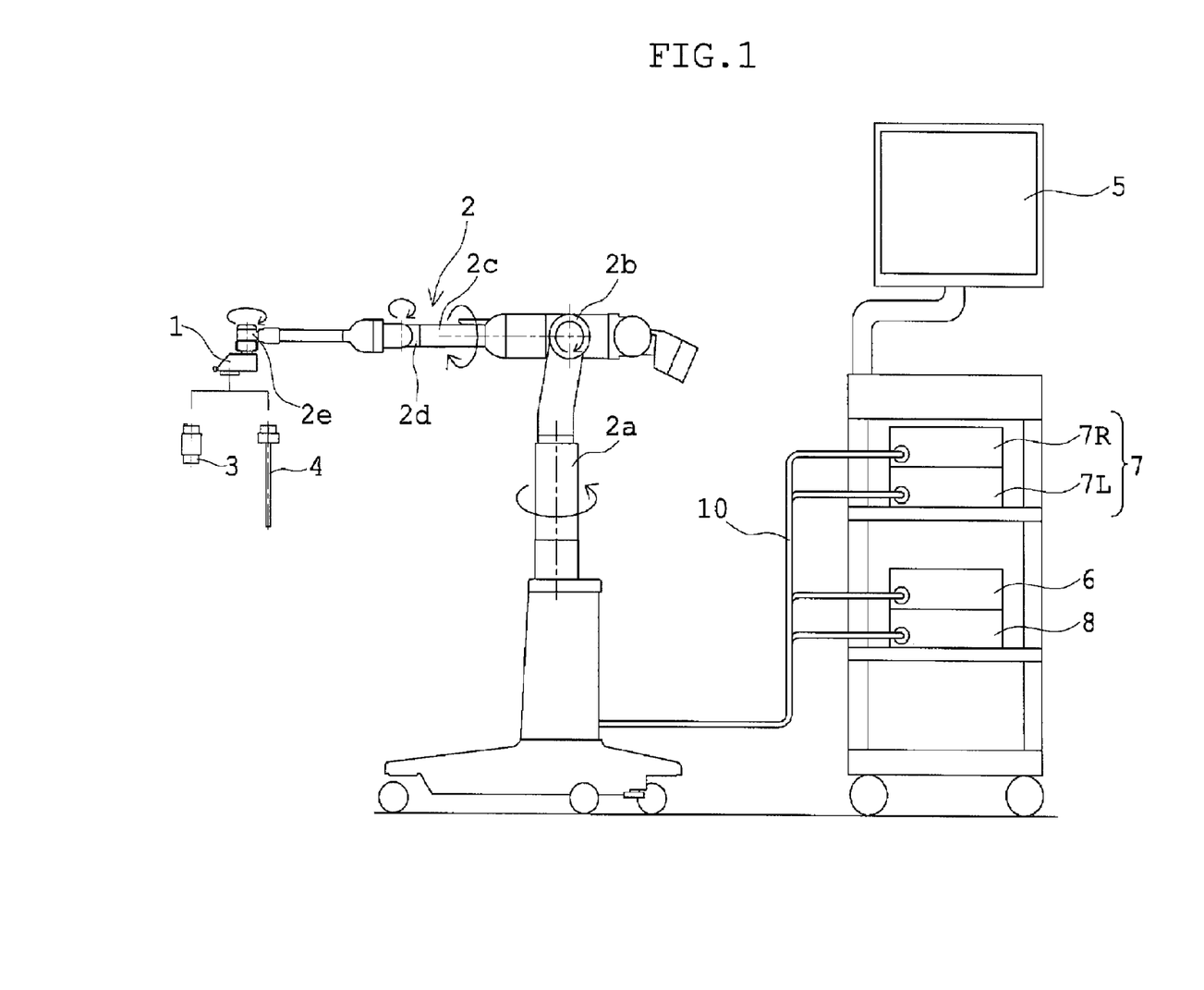
FIG. 1 is a schematic view showing a general arrangement of the surgical observation system according to a first embodiment in the present invention.
Figure 2:
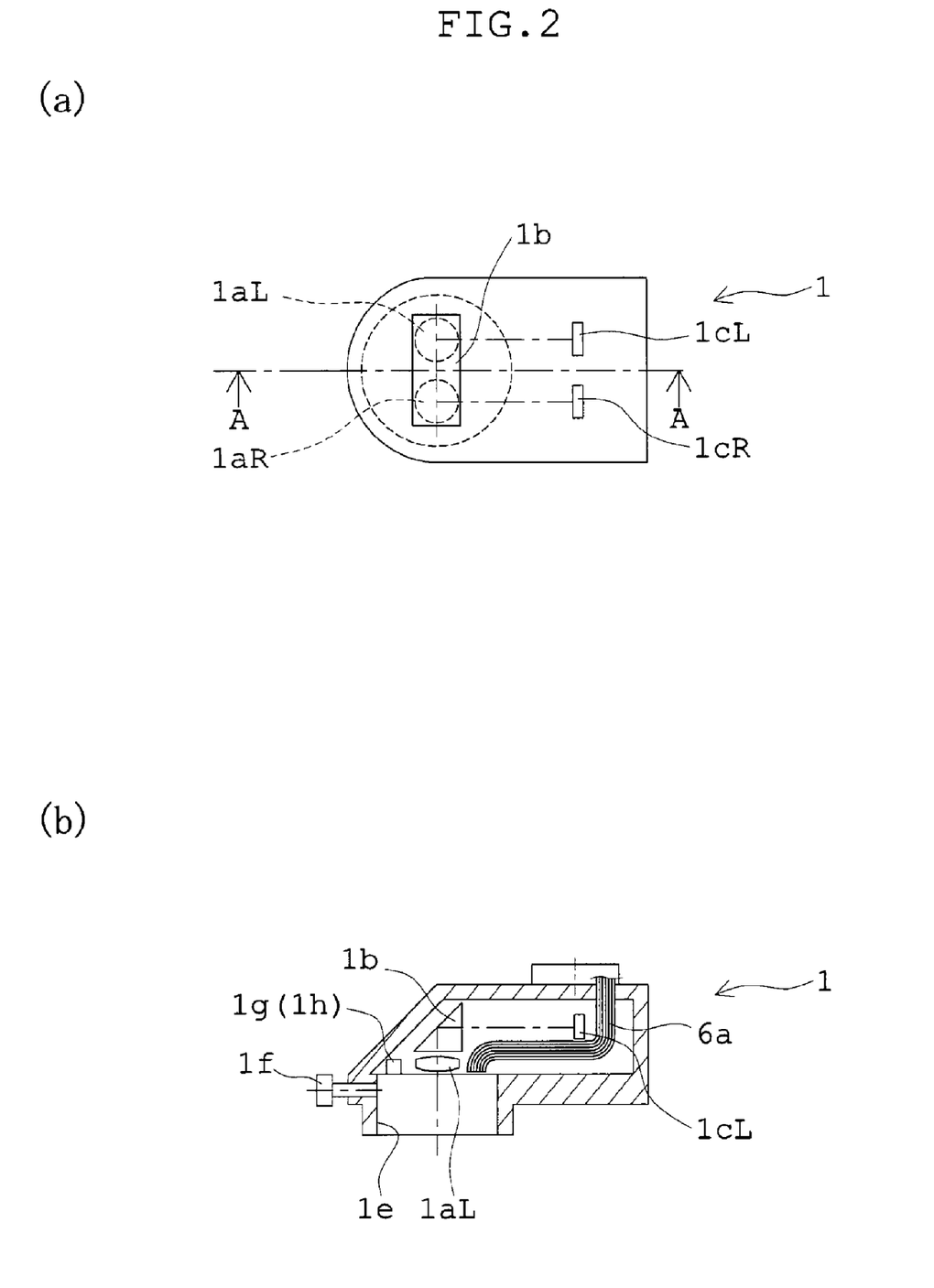
FIG. 2 is explanatory views showing the structure of the mounting and dismounting section provided with essential parts of the surgical observation system of FIG. 1, in which (a) is a plan view showing an internal optical arrangement and (b) is a sectional view taken along line A-A of (a).
Figure 3:
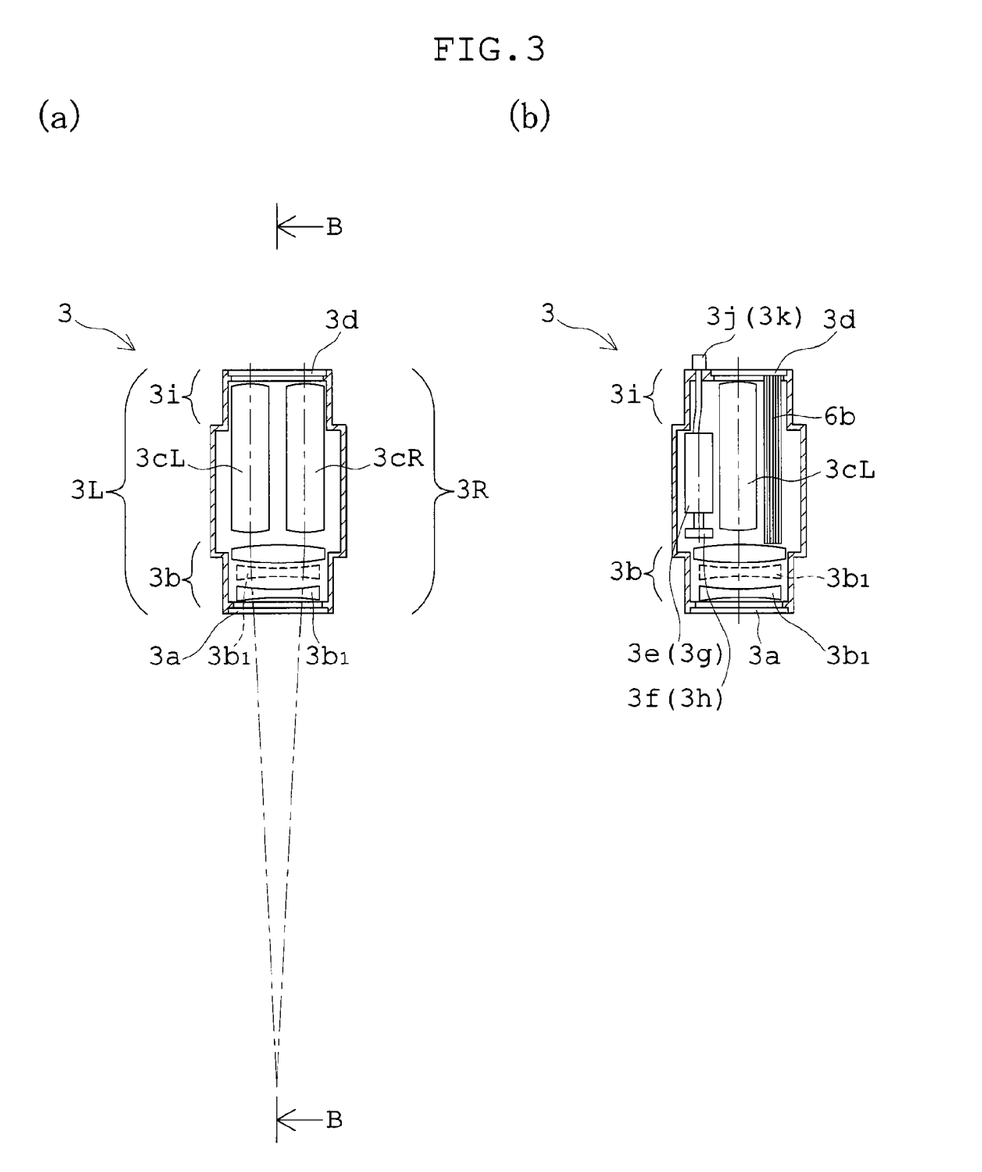
FIG. 3 is explanatory views showing the structure of the microscope objective unit provided with essential parts of the surgical observation system of FIG. 1, in which (a) is a sectional view looking from a position where a pair of optical paths is shown and (b) is a sectional view taken along line B-B of (a).
Figure 4:
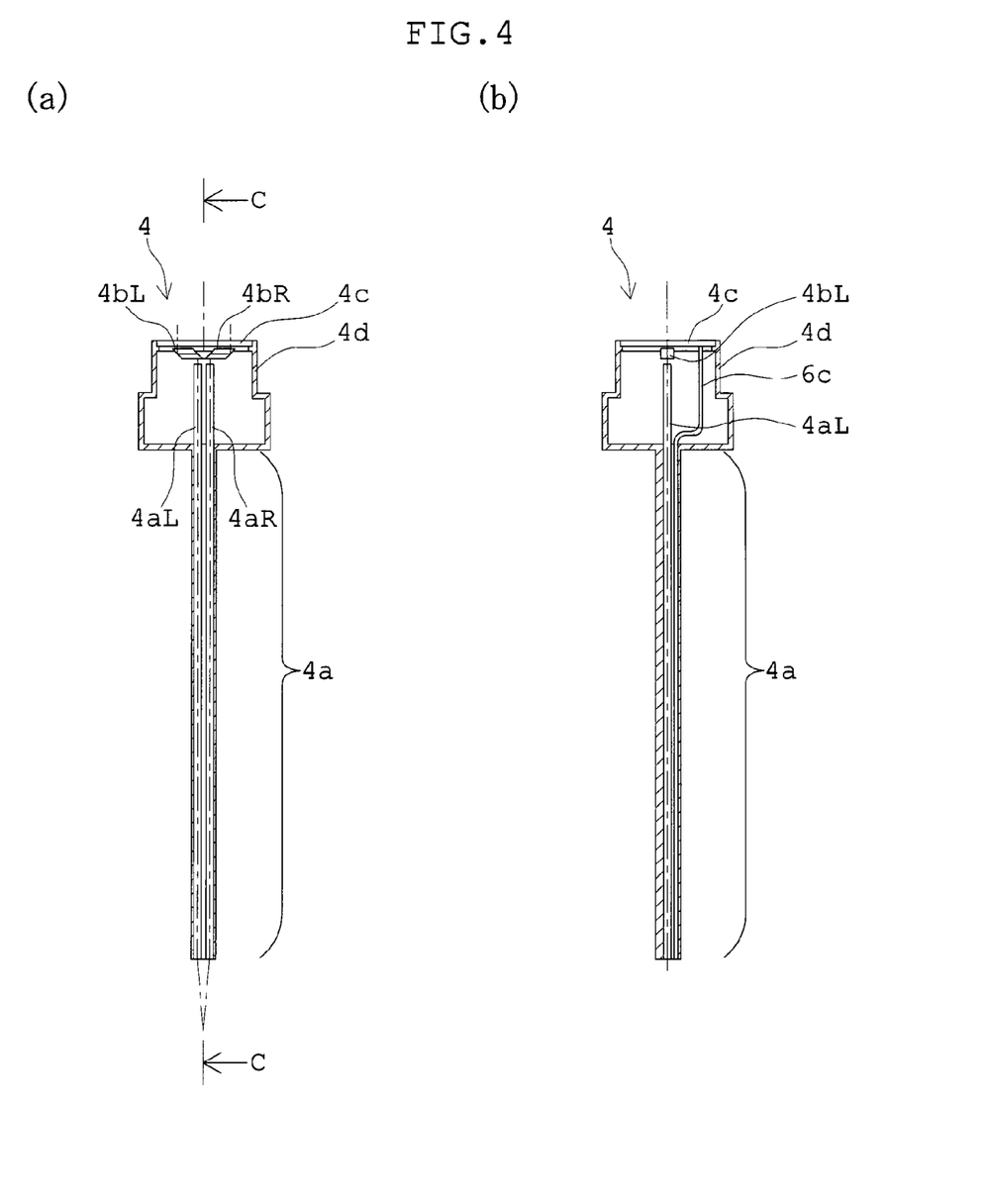
FIG. 4 is explanatory views showing the structure of the endoscope objective unit provided with essential parts of the surgical observation system of FIG. 1, in which (a) is a sectional view looking from a position where a pair of optical paths is shown and (b) is a sectional view taken along line C-C of (a).
Figure 5:
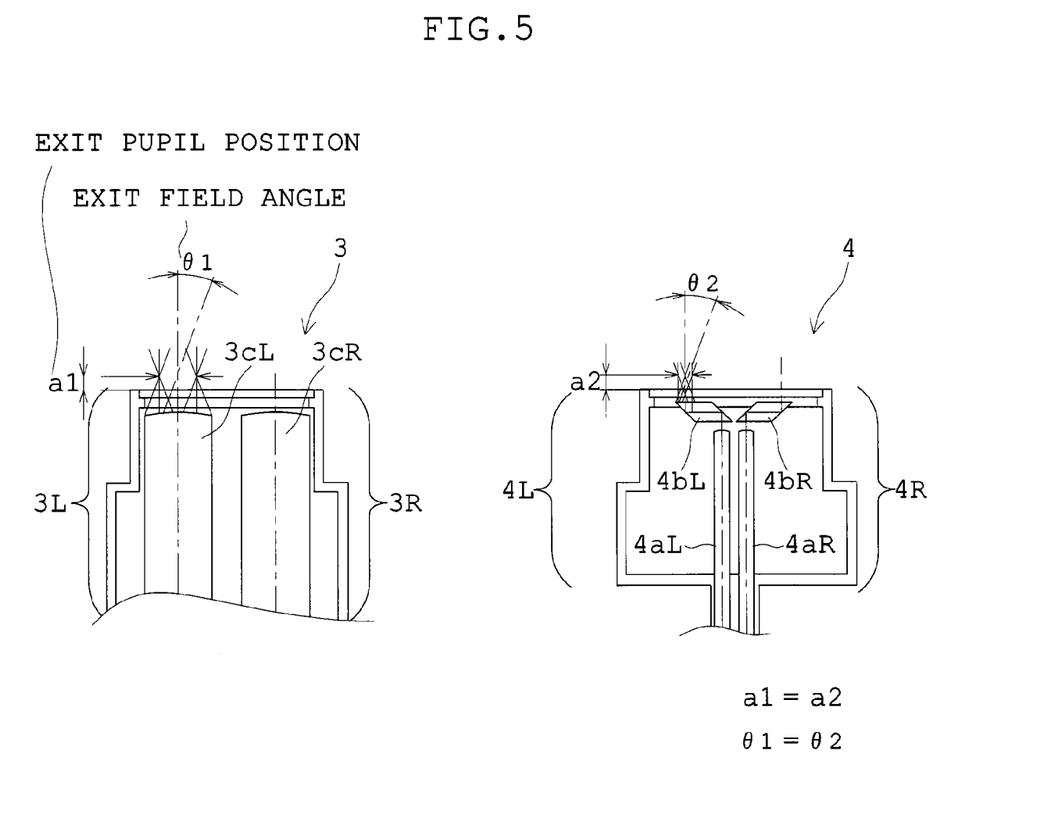
FIG. 5 is an explanatory view showing the exit field angles and exit pupil positions of the mountable and dismountable endoscope objective unit and microscope objective unit in the surgical observation system of the first embodiment.
Figure 6:
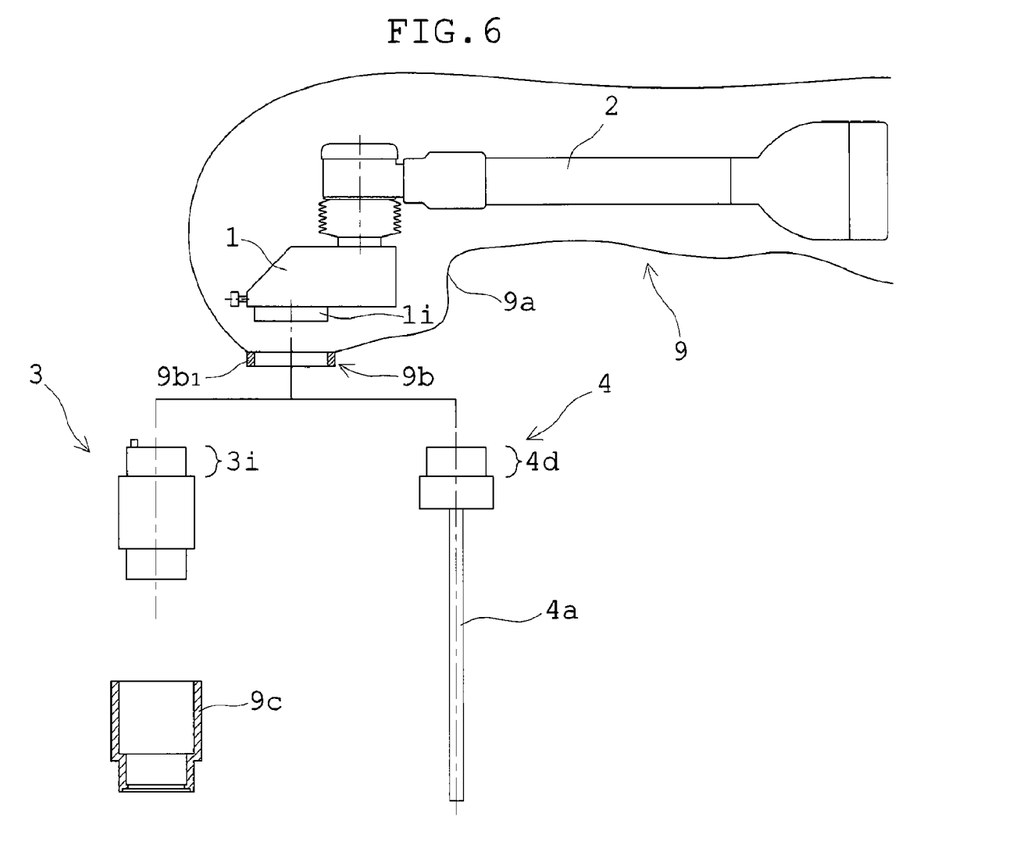
FIG. 6 is an explanatory view showing an example of a means for keeping off the infection of bacteria in the case where the surgical observation system of the first embodiment is used and the surgical operation is actually performed.

FIG. 1 is a schematic view showing a general arrangement of the surgical observation system according to the first embodiment in the present invention, and FIG. 2 is explanatory views showing the structure of the mounting and dismounting section provided with essential parts of the surgical observation system of FIG. 1, in which (a) is a plan view showing an internal optical arrangement and (b) is a sectional view taken along line A-A of (a). FIG. 3 is explanatory views showing the structure of the microscope objective unit provided with essential parts of the surgical observation system of FIG. 1, in which (a) is a sectional view looking from a position where a pair of optical paths is shown and (b) is a sectional view taken along line B-B of (a). FIG. 4 is explanatory views showing the structure of the endoscope objective unit provided with essential parts of the surgical observation system of FIG. 1, in which (a) is a sectional view looking from a position where a pair of optical paths is shown and (b) is a sectional view taken along line C-C of (a). FIG. 5 is an explanatory view showing the exit field angles and exit pupil positions of the mountable and dismountable endoscope objective unit and microscope objective unit in the surgical observation system of the first embodiment. FIG. 6 is an explanatory view showing an example of a means for keeping off the infection of bacteria in the case where the surgical observation system of the first embodiment is used and the surgical operation is performed.

The surgical observation system of the first embodiment, as shown in FIG. 1, includes a supporting arm 2 provided with a mounting and dismounting section 1, a microscope objective unit 3 and an endoscope objective unit 4 which are mountable and dismountable with respect to the mounting and dismounting section 1, a display device 5, an illumination light source 6, an image processing control device 7, and a driving control device 8. The surgical observation system of the first embodiment is constructed so that the microscope objective unit 3 or the endoscope objective unit 4 constitutes an observation apparatus together with the mounting and dismounting section 1, and the microscope objective unit 3 and the endoscope objective unit 4 are selectively mounted to the mounting and dismounting section 1 and thereby the changeover between the microscope observation and the endoscope observation can be made. The supporting arm 2 has a plurality of articulation parts 2a-2e and is constructed so that the microscope objective unit 3 or the endoscope objective unit 4 mounted to the mounting and dismounting section 1 can be moved in the three-dimensional direction.

The mounting and dismounting section 1, as shown in FIG. 2(a), is provided with a pair of imaging lenses 1aL and 1aR and a pair of image sensors 1cL and 1cR in the interior thereof. Each of the image sensors 1cL and 1cR is constructed with a CCD, for instance. The imaging lens 1aL and the image sensor 1cL constitute an image pickup optical system for the left eye, while the imaging lens 1aR and the image sensor 1cR constitute an image pickup optical system for the right eye. Also, in FIG. 2(a), reference numeral 1b represents a path bending prism bending emergent optical axes from the imaging lenses 1aL and 1aR toward the image sensors 1cL and 1cR.

The mounting and dismounting section 1, as shown in FIG. 2(b), is provided with a mounting and dismounting port 1e constructed so that the microscope objective unit 3 and the endoscope objective unit 4 are mountable and dismountable by having interchangeability. On the side of the mounting and dismounting port 1e is provided a fixed screw 1f which ensures a mounted state where the microscope objective unit 3 or the endoscope objective unit 4 is mounted to the mounting and dismounting port 1e. In the inner part of the mounting and dismounting port 1e, a female connector 1g (1h) is provided for bringing a focusing optical system driving motor 3e and a variable magnification optical system driving motor 3g of the microscope objective unit 3 to energized states by coming in contact with a male connector 3j (3k) described later, when the microscope objective unit 3 is mounted.

In the interior of the mounting and dismounting section 1, one end of a light guide 6a is placed as a light guiding means for introducing illumination light emitted from the illumination light source 6 shown in FIG. 1 into an observation object.

The microscope objective unit 3, as illustrated in FIG. 3(a), includes a pair of microscope objective optical systems 3L and 3R constructed to have a focusing optical system 3b and a pair of variable magnification optical systems 3cL and 3cR in the interior thereof. In this way, the focusing optical system 3b and the variable magnification optical system 3cL for the left eye constitute the microscope objective optical system 3L for the left eye, while the focusing optical system 3b and the variable magnification optical system 3cR for the right eye constitute the microscope objective optical system 3R for the right eye. Also, in FIG. 3, reference numerals 3a and 3d denote cover glasses.

The pair of microscope objective optical systems 3L and 3R is constructed to make the afocal light beams emerge therefrom toward the mounting and dismounting section 1. The pair of variable magnification optical systems 3cL and 3cR is arranged to be in optical alignment on the optical axes with the pair of imaging lenses 1aL and 1aR in the mounting and dismounting section 1 in a state where the microscope objective unit 3 is mounted to the mounting and dismounting section 1.

In addition, the microscope objective unit 3, as shown in FIG. 3(b), has the focusing optical system driving motor 3e and a focusing optical system driving gear 3f for driving the focusing optical system 3b. The focusing optical system driving motor 3e receives a focusing control signal from the driving control device 8 shown in FIG. 1 in the energized state, thereby rotating the focusing optical system driving gear 3f in a preset direction by a preset amount. The focusing optical system driving gear 3f is engaged with a cam provided on a lens frame (omitted from the figure) of the focusing optical system 3b and is rotated to thereby move a preset lens (here, a lens $3b_1$) constituting the focusing optical system 3b held on the lens frame (omitted from the figure) in the direction of the optical axis by a preset amount.

The microscope objective unit 3 further has the variable magnification optical system driving motor 3g and a variable magnification optical system driving gear 3h for driving the pair of variable magnification optical systems 3cL and 3cR on the far side of the focusing optical system driving motor 3e and the focusing optical system driving gear 3f. The variable magnification optical system driving motor 3g receives a magnification change control signal from the driving control device 8 shown in FIG. 1 in the energized state, thereby rotating the variable magnification optical system driving gear 3h in a preset direction by a preset amount. The variable magnification optical system driving gear 3h is engaged with a cam provided on a lens frame (omitted from the figure) of the pair of variable magnification optical systems 3cL and 3cR and is rotated to thereby move preset lenses constituting the pair of variable magnification optical systems 3cL and 3cR held on the lens frame along the optical axes by preset amounts.

The microscope objective unit 3 is constructed so that its one end 3i can be fitted into the mounting and dismounting port 1e of the mounting and dismounting section 1. The one end 3i of the microscope objective unit 3 is provided with the male connector 3j (3k) for bringing the focusing optical system driving motor 3e and the variable magnification optical system driving motor 3g to energized states by coming in contact with the female connector 1g (1h). In the interior of the microscope objective unit 3, a light guide 6b is provided as a light guiding means for introducing illumination light emitted from the illumination light source 6 shown in FIG. 1 and passing through the light guide 6a shown in FIG. 2 into the observation object. The light guide 6b is optically connected with the light guide 6a in a state where the microscope objective unit 3 is mounted to the mounting and dismounting port 1e and is placed so that illumination light emerging from the object-side end surface of the light guide 6b is introduced into the focusing optical system 3b.

The endoscope objective unit 4, as shown in FIG. 4 (a), is provided with a pair of objective optical system 4L and 4R constructed to have a tubular insertion section 4A in the interior thereof. In the tubular insertion section 4a, a pair of relay optical systems 4aL and 4aR is arranged. The pair of relay optical system 4aL and 4aR is constructed to make the afocal light beams emerge therefrom toward the mounting and dismounting section 1. A pair of parallelogram prisms 4bL and 4bR is arranged on the mounting-and-dismounting-section-1 side of the relay optical systems 4aL and 4aR. The parallelogram prisms 4bL and 4bR widens a spacing between emergent optical axes from the relay optical systems 4aL and 4aR toward the mounting and dismounting section 1 so that, in a state where the endoscope objective unit 4 is mounted to the mounting and dismounting section 1, afocal light beams emerging from the relay optical systems 4aL and 4aR are optically aligned on the optical axes with the pair of imaging optical systems 1aL and 1aR in the mounting and dismounting section 1. The relay optical system 4aL for the left eye and the parallelogram prism 4bL for the left eye constitute the endoscope objective optical system 4L for the left eye, while the relay optical system 4aR for the right eye and the parallelogram prism 4bR for the right eye constitute the endoscope objective optical system 4R for the right eye. Also, in FIG. 4, reference numeral 4c denotes a cover glass. The endoscope objective unit 4 is constructed so that its one end 4d can be fitted into the mounting and dismounting port 1e of the mounting and dismounting section 1. As shown in FIG. 4(b), a light guide 6c runs inside the endoscope objective unit 4 for introducing illumination light from the illumination light source 6 to an object to be observed. The light guide 6c is configured to be optically connected with the light guide 6a when the endoscope objective unit 4 is mounted to the mounting and dismounting port 1e of the mounting and dismounting section 1.

The surgical observation system of the first embodiment, as illustrated in FIG. 5, is constructed so that exit pupil positions a1 and exit field angles θ1 in the pair of microscope objective optical systems 3L and 3R of the microscope objective unit 3 become equal to exit pupil positions a2 and exit field angles θ2 in the pair of endoscope objective optical systems 4L and 4R of the endoscope objective unit 4, respectively.

Moreover, the surgical observation system of the first embodiment, as shown in FIG. 6, is such that a sterilization drape 9 is provided to be mountable and dismountable with respect to the supporting arm 2 provided with the mounting and dismounting section 1. The sterilization drape 9 includes a drape part 9a and a drape cap 9b. The drape part 9a is constructed to cover the supporting arm 2. The drape cap 9b has an opening 9b1 into which a periphery 1i of the mounting and dismounting port 1e in the mounting and dismounting section 1 can be fitted. The drape part 9a is such that its one end is integrally connected to the drape cap 9b along the contour of the opening 9b1.

By mounting the drape cap 9b to the periphery 1i of the mounting and dismounting section 1 and covering the supporting arm 2 with the drape part 9a, a sterilization means is used for the supporting arm 2 provided with the mounting and dismounting section 1. Also, the drape cap 9b is provided with the opening 9b1 and the mounting and dismounting port 1e of the mounting and dismounting section 1 is not covered. Consequently, in a state where the drape 9 is mounted to the supporting arm 2, the microscope objective unit 3 or the endoscope objective unit 4 can be mounted to, and dismounted from, the mounting and dismounting section 1.

On the other hand, the microscope objective unit 3 and the endoscope objective unit 4 are such that sterilization treatment, such as autoclaving or EOG, is applied independently and thereby the infection of bacteria to the patient in the peripheral part of the observation apparatus in the surgical observation system can be prevented. Also, the microscope objective unit 3, in contrast with the endoscope objective unit 4, does not have the insertion section inserted in the body of the patient. Hence, instead of applying the sterilization treatment, such as autoclaving or EOG, to the whole of the microscope objective unit 3, a sterilization cover 9c configured so that the periphery of the microscope objective unit 3 is fitted may be provided to be mountable and dismountable with respect to the microscope objective unit 3.

As for the rest, the display device 5 is connected with the image processing control device 7 through wiring in a cable 10 and is constructed to display three-dimensional images which are picked up by the image sensors 1cL and 1cR and to which preset signal processing is applied by the image processing control device 7. The illumination light source 6 is the light source emitting light for illuminating the observation object and is connected to the light guide 6a provided in the cable 10.

The image processing control device 7 is constructed with a pair of camera control units (CCUs) 7L and 7R provided corresponding to the image sensors 1cL and 1cR. The pair of camera control units (CCUs) 7L and 7R is connected with the image sensors 1cL and 1cR in the mounting and dismounting section 1 and the display device 5 through the wiring in the cable 10 and has functions of driving the image sensors 1cL and 1cR, applying preset processing to two imaging signals with parallax from the image sensors 1cL and 1cR, and displaying the three-dimensional images synthesized, on the display device 5.

The driving control device 8 is connected with the female connectors 1g and 1h in the mounting and dismounting section 1 through the wiring in the cable 10 and has functions of exercising the driving control of the focusing optical system driving motor 3e of the focusing optical system 3b and the driving control of the variable magnification optical system driving motor 3g of the variable magnification optical systems 3cL and 3cR, for example, in the case where the microscope objective unit 3 is mounted to the mounting and dismounting section 1 and the energized state is brought about.

According to the surgical observation system of the first embodiment constructed as described above, one of the microscope objective unit 3 and the endoscope objective unit 4 is selected and is mounted to the mounting and dismounting section 1 provided in the supporting arm 2, and thereby the changeover between the microscope observation and the endoscope observation can be facilitated. When the microscope observation is switched to the endoscope observation, the optical arrangement of the microscope objective unit 3 unnecessary for the endoscope observation does not remain on the optical path. According to the surgical observation system of the first embodiment, therefore, when the endoscope observation is carried out, the observation apparatus, in contrast with the conventional observation apparatuses such as those described in Kokai Nos. Hei 6-167658 and 2005-134537, is capable of materially reducing the length in the observation direction so that a compact design is achieved, and is capable of exceptionally improving the maneuverability where the apparatus is moved through the supporting arm.

In the surgical observation system, the microscope objective unit 3 and the endoscope objective unit 4 are constructed to be mountable and dismountable by having interchangeability in respect of the mounting and dismounting section 1 including the imaging optical systems and the image sensors. Hence, as shown in FIG. 6, the sterilization drape 9 provided with the opening 9b1 so that the endoscope objective unit 4 or the microscope objective unit 3 can be mounted to the periphery 1i of the mounting and dismounting port 1e of the mounting and dismounting section 1 is provided to be mountable and dismountable and the sterilization means can be used independently for the endoscope objective unit 4 or the microscope objective unit 3. As a result, when the changeover from the microscope observation to the endoscope observation is performed, it becomes unnecessary to remove the drape covering the mounting and dismounting section, unlike the conventional observation apparatuses such as those described in Kokai Nos. Hei 6-167658 and 2005-134537. Thus, the changeover work is not complicated, and there is no need to interrupt the surgical operation.

In the surgical observation system of the first embodiment, individual objective optical systems provided in the endoscope objective unit 4 and the microscope objective unit 3 are constructed so that their exit pupil positions and exit field angles are practically identical. Thus, even when either of the objective units is mounted to the mounting and dismounting section 1, the imaging areas become identical and can be made to coincide with the imaging regions on the image sensors 1cL and 1cR and hence an image loss is not produced. Consequently, it is not necessary that the means making adjustment so that the area of the image formed on each of the image sensors has a preset size is provided in the mounting and dismounting section, and the changeover between the microscope observation and the endoscope observation can be more smoothly performed.

Second Embodiment

Figure 7:
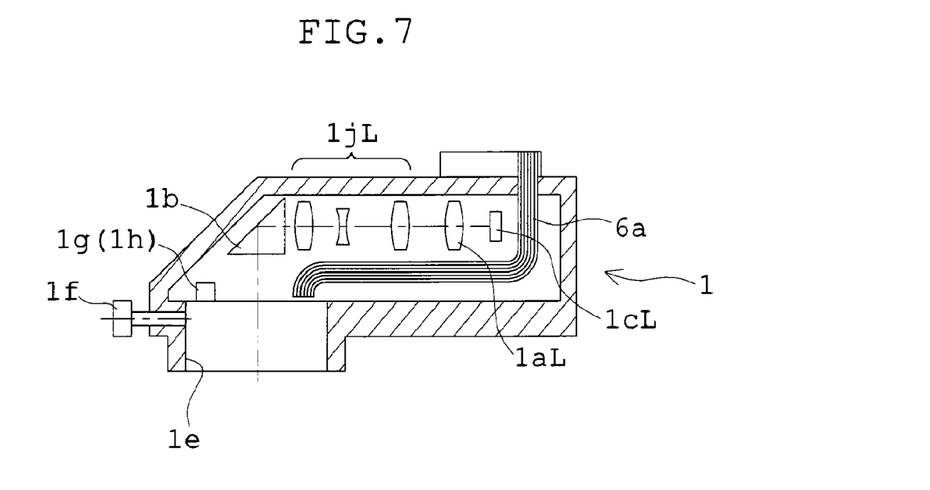
FIG. 7 is a sectional view showing the structure of the mounting and dismounting section of the surgical observation system according to a second embodiment in the present invention, looking from the same side as in FIG. 2(b).

FIG. 7 is a sectional view showing the structure of the mounting and dismounting section of the surgical observation system according to the second embodiment in the present invention, looking from the same side as in FIG. 2(b). In the surgical observation system of the second embodiment, the mounting and dismounting section 1 is provided with a pair of afocal variable magnification optical systems 1jL and 1jR on the object side of the pair of imaging lenses 1aL and 1aR. Also, FIG. 7 is a view showing optical members for the left eye, of a pair of optical members, and thus fails to show the afocal variable magnification optical system 1jR for the right eye and the imaging lens 1aR for the right eye.

The pair of afocal variable magnification optical systems 1jL and 1jR is constructed so that afocal light beams in which the pair of objective optical systems 4L and 4R of the endoscope objective unit 4 is different in magnification from the pair of objective optical systems 3L and 3R of the microscope objective unit 3 can be adjusted to equalize the areas of images formed on the pair of image sensors 1cL and 1cR through the pair of imaging lenses 1aL and 1aR. In the surgical observation system of the second embodiment, the pair of objective optical systems 4L and 4R of the endoscope objective unit 4 and the pair of objective optical systems 3L and 3R of the microscope objective unit 3, even when having different exit pupil positions and exit field angles, are provided to be mountable and dismountable with respect to the mounting and dismounting section 1.

Also, an afocal variable magnification optical system driving motor and an afocal variable magnification optical system driving gear for driving the pair of afocal variable magnification optical systems 1jL and 1jR are provided, although they are omitted from the figure. Their structures are almost the same as in the variable magnification optical system driving motor 3g and the variable magnification optical system driving gear 3h provided in the microscope objective unit 3 of the first embodiment. Specifically, the afocal variable magnification optical system driving motor receives an afocal magnification change control signal from the driving control device 8, thereby rotating the afocal variable magnification optical system driving gear in a preset direction by a preset amount. The afocal variable magnification optical system driving gear is engaged with a cam provided on a lens frame (omitted from the figure) of the pair of afocal variable magnification optical systems 1jL and 1jR and is rotated to thereby move preset lenses constituting the pair of afocal variable magnification optical systems 1jL and 1jR held on the lens frame along optical axes by preset amounts. Other features are almost the same as in the surgical observation system of the first embodiment.

In the surgical observation system of the second embodiment constructed as mentioned above, the pair of afocal variable magnification optical systems 1jL and 1jR is constructed so that afocal light beams in which the endoscope objective unit 4 is different in magnification from the microscope objective unit 3 are adjusted to have the same magnification and can be introduced into the pair of imaging lenses 1aL and 1aR, and the areas of images formed on the pair of image sensors 1cL and 1cR through the pair of imaging lenses 1aL and 1aR can be equalized. According to the surgical observation system of the second embodiment, therefore, the number of degrees of design freedom of the objective optical systems in each of the endoscope objective unit 4 and the microscope objective unit 3 is increased. Other functions and effects are almost the same as in the surgical observation system of the first embodiment.

Third Embodiment

Figure 8:
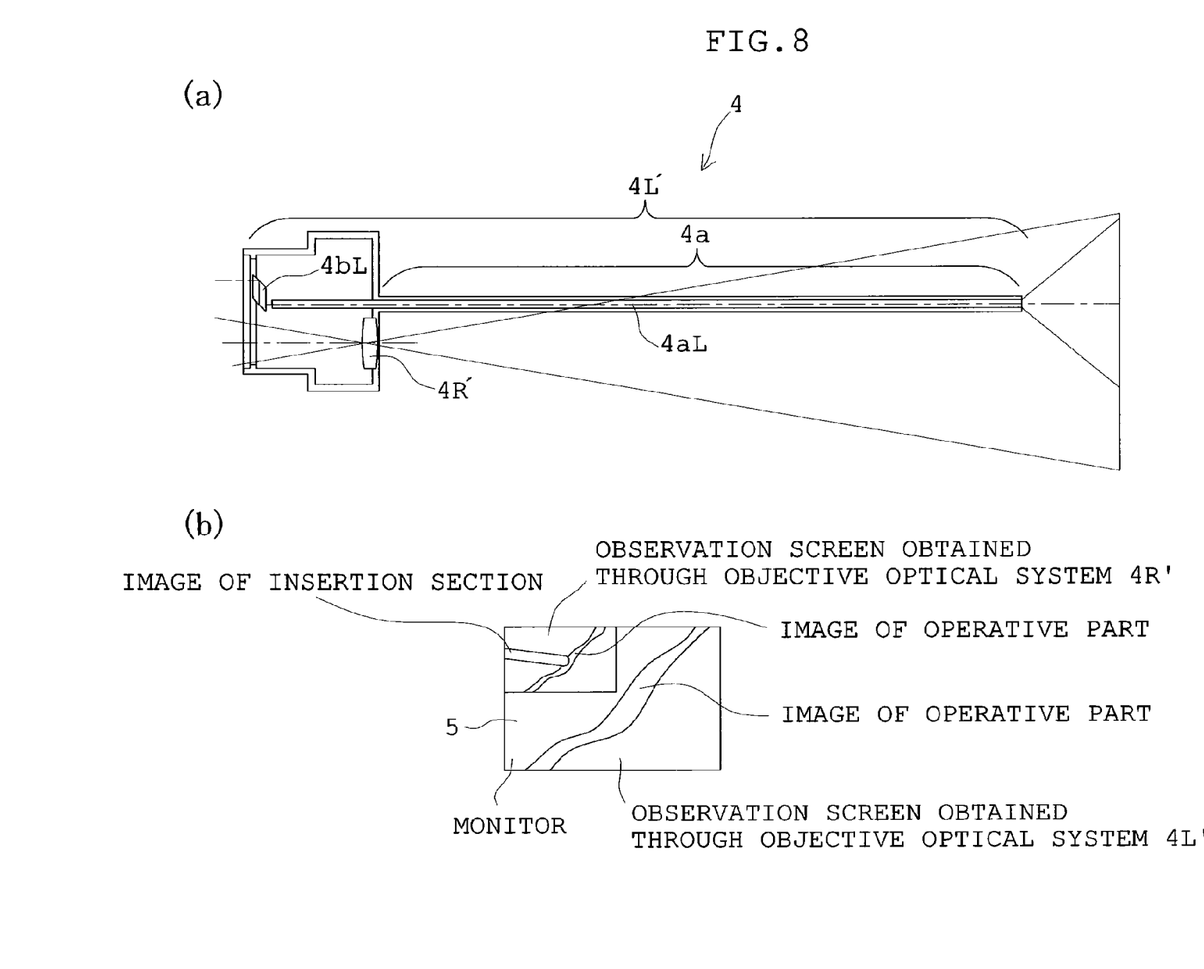
FIG. 8 is explanatory views showing essential parts of the surgical observation system according to a third embodiment in the present invention, in which (a) is a sectional view showing a schematic structure of the endoscope objective unit and (b) is an explanatory view showing a state where observation images obtained through individual objective optical systems in the case where the endoscope objective unit is mounted to the mounting and dismounting section are displayed on a display device.

FIG. 8 is explanatory views showing essential parts of the surgical observation system according to the third embodiment in the present invention, in which (a) is a sectional view showing a schematic structure of the endoscope objective unit and (b) is an explanatory view showing a state where observation images obtained through individual objective optical systems in the case where the endoscope objective unit is mounted to the mounting and dismounting section are displayed on the display device 5. In the surgical observation system of the third embodiment, a pair of objective optical systems 4L' and 4R' in the endoscope objective unit 4 is constructed as two objective optical systems of different observation ranges in size.

Specifically, the objective optical system 4L' of one of the two objective optical systems, like the endoscope objective optical system 4L for the left eye in the first embodiment and the second embodiment, is constructed as the endoscope objective optical system including the relay optical system 4aL encased in the tubular insertion section 4a and the parallelogram prism 4bL. The other objective optical system 4R' is constructed so that an image in a wider observation range than the objective optical system 4L' can be observed, and has the field angle at which the top of the tubular insertion section 4a in the endoscope objective optical system 4L' of a narrower observation range can be viewed. In addition, the other objective optical system 4R' is provided in the proximity of the mounting and dismounting section 1 in the endoscope objective unit 4.

Also, in the third embodiment, the pair of camera control units (CCUs) 7L and 7R of the image processing control device 7 has functions of applying preset processing to two imaging signals of different observation ranges from the image sensors 1cL and 1cR and superimposing an image from the image sensor 1cR on a partial display region in an image from the image sensor 1cL to display these images on the display device 5. Other features are almost the same as in the surgical observation system of each of the first and second embodiments.

According to the surgical observation system of the third embodiment constructed as mentioned above, for example, as shown in FIG. 8(b), an internal micro observation and an external macro observation in the two-dimensional observation can be carried out in such a way that a relative positional relationship between an internal operative part and the insertion section of the endoscope and a condition of the internal operative part are displayed on a display screen and observed at the same time. Other functions and effects are almost the same as in the surgical observation system of each of the first and second embodiments.

Fourth Embodiment

Figure 9:
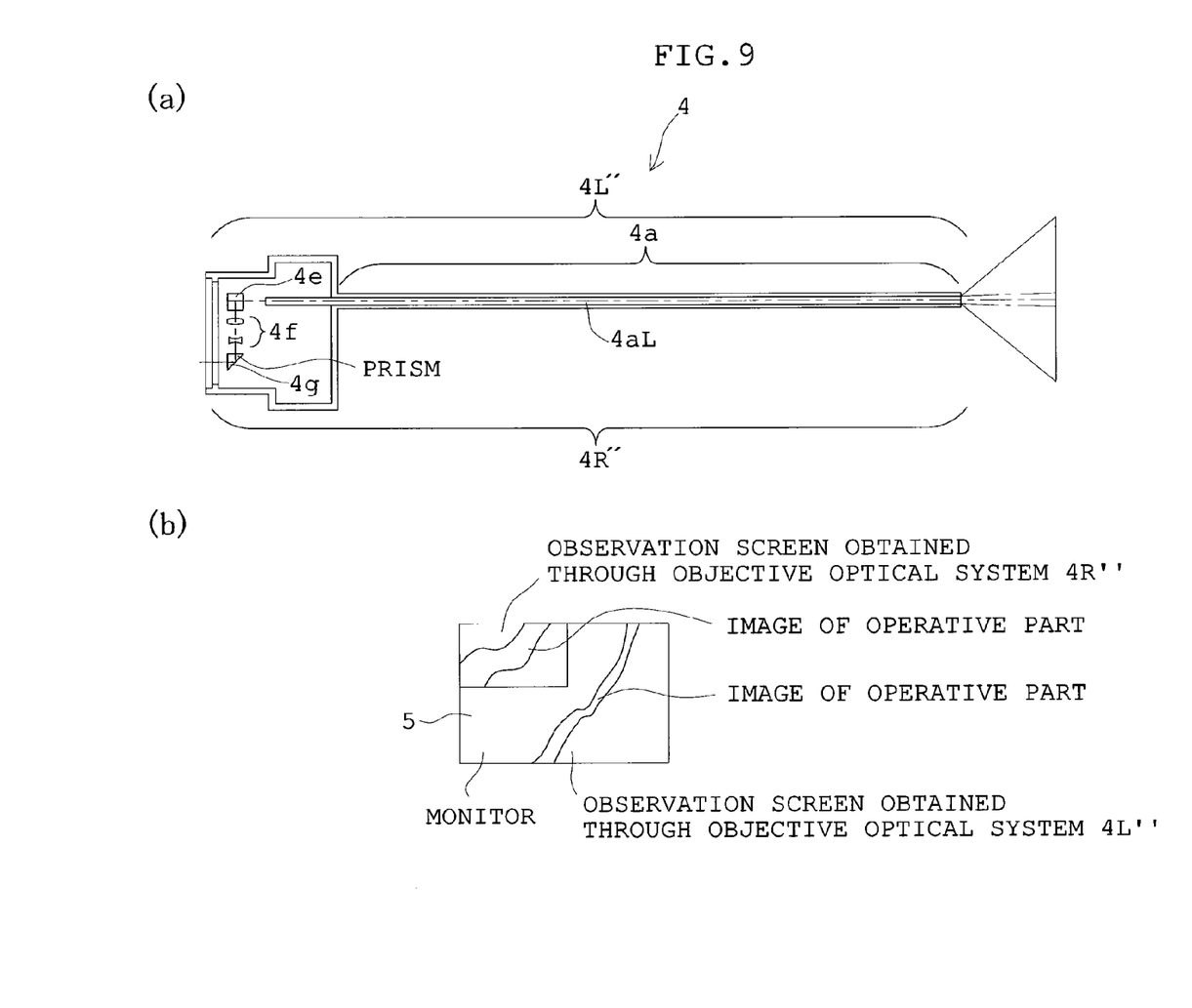
FIG. 9 is explanatory views showing essential parts of the surgical observation system according to a fourth embodiment in the present invention, in which (a) is a sectional view showing a schematic structure of the endoscope objective unit and (b) is an explanatory view showing a state where observation images obtained through individual objective optical systems in the case where the endoscope objective unit is mounted to the mounting and dismounting section are displayed on a display device

FIG. 9 is explanatory views showing essential parts of the surgical observation system according to the fourth embodiment in the present invention, in which (a) is a sectional view showing a schematic structure of the endoscope objective unit and (b) is an explanatory view showing a state where observation images obtained through individual objective optical systems in the case where the endoscope objective unit is mounted to the mounting and dismounting section are displayed on the display device 5. In the surgical observation system of the fourth embodiment, a pair of objective optical systems 4L" and 4R" in the endoscope objective unit 4 is constructed as two objective optical systems of different observation ranges in size.

Specifically, the two objective optical systems are constructed to have the relay optical system 4aL encased in the tubular insertion section 4a; a path splitting member (for example, a beam splitter) 4e placed on the mounting and dismounting section side of the relay optical system 4aL; an optical system 4f narrowing the observation range, placed on one optical path split through the path splitting member 4e; and a path deflecting member (for example, a prism) 4g. The relay optical system 4aL and the transmission side of the path splitting member 4e constitute the objective optical system 4L" in which the observation range is relatively wide, while the relay optical system 4aL, the reflection side of the path splitting member 4e, the optical system 4f narrowing the observation range, and the path deflecting member 4g constitute the objective optical system 4R" in which the observation range is relatively narrow.

Also, in the fourth embodiment, the pair of camera control units (CCUs) 7L and 7R of the image processing control device 7 has functions of applying preset processing to two imaging signals of different observation ranges from the image sensors 1cL and 1cR and superimposing an image from the image sensor 1cL on a partial display region in an image from the image sensor 1cR to display these images on the display device 5. Other features are almost the same as in the surgical observation system of each of the first and second embodiments.

According to the surgical observation system of the fourth embodiment constructed as mentioned above, for example, as shown in FIG. 9(b), an internal micro observation and an external macro observation in the two-dimensional observation can be carried out in such a way that a detailed condition presented in the proximity of an internal operative part and a condition on the periphery of the internal operative part are displayed on a display screen and observed at the same time. Other functions and effects are almost the same as in the surgical observation system of each of the first and second embodiments.

Industrial Applicability

The present invention is useful for a surgical field in which both the endoscope observation and the microscope observation are required for the surgical operation, for example, in neurosurgery.

The invention claimed is:

1. A surgical observation system comprising:
an observation apparatus switchable between an endoscope observation and an microscope observation; and
a supporting arm movable in a three-dimensional direction in a state where the observation apparatus is supported,
wherein the observation apparatus is constructed to include an endoscope objective unit having a tubular insertion section and provided with objective optical systems; a microscope objective unit provided with objective optical systems having a focusing optical system and variable magnification optical systems; and a mounting and dismounting section provided in the supporting arm, having a mounting and dismounting port constructed so that the endoscope objective unit and the microscope objective unit are mountable and dismountable by having interchangeability, wherein the objective optical systems provided in each of the endoscope objective unit and the microscope objective unit are constructed so that light beams emerging therefrom toward the mounting and dismounting section are changed to afocal light beams, wherein the mounting and dismounting section is provided with a pair of imaging lenses and a pair of image sensors and is constructed so that, in a state where a selected one of the endoscope objective unit and the microscope objective unit is mounted to the mounting and dismounting port of the mounting and dismounting section, the afocal light beams, emerging from the objective optical systems in the selected one of the endoscope objective unit and the microscope objective unit, are optically connected with the imaging lenses and the image sensors, wherein the objective optical systems in the endoscope objective unit are constructed as a pair of objective optical systems of different observation ranges in size so that, in a state where the endoscope objective unit is mounted to the mounting and dismounting port of the mounting and dismounting section, a pair of afocal light beams emerging from the pair of objective optical systems in the endoscope objective unit are optically connected with the pair of imaging optical systems and the pair of image sensors provided in the mounting and dismounting section, wherein, of the pair of objective optical systems of different observation ranges in size, arranged in the endoscope objective unit, an objective optical system with a narrower observation range is constructed as an endoscope objective optical system having the tubular insertion section, and wherein, of the pair of objective optical systems of different observation ranges in size, arranged in the endoscope objective unit, an objective optical system with a wider observation range has a field angle at which a top of the tubular insertion section in the objective optical system with the narrower observation range is observable, and is provided in a proximity of the mounting and dismounting section in the endoscope objective unit.

2. A surgical observation system according to claim 1, wherein the supporting arm is provided with a sterilization drape mountable and dismountable, having an opening mountable on a periphery of the mounting and dismounting port in the mounting and dismounting section, and each of the endoscope objective unit and the microscope objective unit is constructed so that a sterilization means can be taken independently.

3. A surgical observation system according to claim 2, wherein the microscope objective unit is provided with a sterilization cover to be mountable and dismountable.

4. A surgical observation system according to claim 1, wherein the objective optical systems provided in the endoscope objective unit and the objective optical systems provided in the microscope objective unit are constructed to be practically identical in exit pupil positions and exit field angles.

5. A surgical observation system according to claim 1, wherein the objective optical systems of the microscope objective unit are constructed as a pair of microscope objective optical systems including the focusing optical system placed in common with two optical paths with parallax and a pair of variable magnification optical systems arranged in the two optical paths with parallax so that, in a state where the microscope objective unit is mounted to the mounting and dismounting port of the mounting and dismounting section, a pair of afocal light beams emerging from the pair of microscope objective optical systems is optically connected with the pair of imaging optical systems and the pair of image sensors provided in the mounting and dismounting section.

6. A surgical observation system according to claim 1, wherein the mounting and dismounting section is provided with a pair of afocal variable magnification optical systems on an object side of the pair of imaging optical systems.

* * * * *